US006316189B1

(12) United States Patent
Haddad et al.

(10) Patent No.: US 6,316,189 B1
(45) Date of Patent: Nov. 13, 2001

(54) EVALUATION OF CHANGES IN BREAST CELLS USING NIPPLE ASPIRATE FLUID

(75) Inventors: Bassem R. Haddad, Rockville; Robert B. Dickson, Silver Spring, both of MD (US); Stephen J. McCormack, Sag Harbor, NY (US)

(73) Assignee: Georgetown University School of Medicine, Washington, DC (US)

( * ) Notice: Subject to any disclaimer, the term of this patent is extended or adjusted under 35 U.S.C. 154(b) by 0 days.

(21) Appl. No.: 09/176,928

(22) Filed: Oct. 23, 1998

Related U.S. Application Data

(60) Provisional application No. 60/062,775, filed on Oct. 24, 1997.

(51) Int. Cl.[7] .............................. C12Q 1/68; C12P 19/34; C12N 5/08; C12N 15/12
(52) U.S. Cl. ............................. 435/6; 435/91.2; 435/378; 536/24.31
(58) Field of Search .............................. 435/6, 378, 91.2; 536/24.31

(56) References Cited

PUBLICATIONS

Kelsey et al. Epidemiology and prevention of breast cancer. Annu. Rev. Public Health vol. 17 pp. 47–67, 1966.*
Gray et al. Molecular cytogenetics of human breast cancer. Cold Spring Symp. Quant. Biol. vol. 59 pages 645–652, 1994.*
Telenius et al. Degenerate oligonucleotide–primed PCR: General amplification of target DNA by a single degenerate primer. Genomics vol. 13 pp. 718–725, 1992.*
Buehring et al. Growth rates of normal and abnormal human mammary epithelia in cell culture. Cancer Res. vol. 36 pp. 3742–3747, 1976.*
Bano et al. Production and characterization of mammary–derived growth factor 1 in mammary epithelial cell lines. Biochemistry vol. 31 pp. 610–616, 1992.*

* cited by examiner

*Primary Examiner*—John S. Brusca
(74) *Attorney, Agent, or Firm*—Robin L. Teskin

(57) ABSTRACT

This invention provides a method for studying chromosomal gains and losses in cells from nipple aspirate fluid comprising the steps of: (1) aspirating fluid from breasts; (2) placing the samples of fluid obtained in step 1 onto dishes containing conditioned medium composed of a mixture of (a) supernatant from immortalized mammary epithelial cells and (b) mammary epithelial growth medium; (3) incubating the product of step 2 in a humidified incubator; (4) replenishing the medium in the dishes prepared in step 2 at regular intervals to maintain cell growth; (5) isolating the cells from the cultures; (6) preparing DNA from these cells; (7) amplifying the DNA; (8) labeling an aliquot of the amplified DNA; and (9) evaluating the labeled DNA for evidence of chromosomal gains or losses.

6 Claims, No Drawings

EVALUATION OF CHANGES IN BREAST CELLS USING NIPPLE ASPIRATE FLUID

This application claims the benefit of Provisional Patent Application Ser. No. 60,062,775 filed Oct. 24, 1997.

FIELD OF THE INVENTION

This invention is related to the detection of chromosomal changes in memory epithelial cells obtained from nipple aspirate fluid as a screening tool for premalignant and malignant breast lesions.

BACKGROUND OF THE INVENTION

The increased availability of testing for breast cancer predisposing gene mutations (e.g. BRCA1 and BRCA2) will soon result in a major increase in the number of young women identified as mutation carriers who require early and continuous surveillance. Means for early detection of chromosomal changes in women, especially those with family history of mutations, is needed. Mammography alone may not be sufficient for such evaluation. The effectiveness of mammography has not been established in women younger than 40 years of age. Younger women have more dense breast tissue, with reduced mammographic sensitivity. Moreover, tumor growth rates are often higher in younger women, thereby necessitating more frequent screening. However, carriers of some mutations (such as ataxia telangiectasia) may have increased sensitivity to radiation and could, conceivably, be harmed by frequent mammograms. Hence, new means of evaluation which avoid exposure to radiation would be particularly appropriate for use in younger women.

Nipple aspirate fluid (NAF) is secreted continuously by the non-lactating breast and, in 50% to 70% of premenopausal women, can be aspirated through duct openings in the nipple using a simple non-invasive pump. NAF is of interest because it has a relatively long retention time in the breast alveolar-ductal system, where it accumulates exfoliated mammary epithelial cells. Thus, cytogenetic examination of cells found in NAF would provide a "snapshot" of the micro-environment where breast cancer originates.

To date, classical cytologic assessment has been used to identify abnormalities in NAF-derived cells as an indicator of early progression toward breast cancer. However, NAF cytology alone is not sufficiently sensitive to identify the subgroup of women who are on a progression pathway that will lead to breast cancer. Atypical epithelial cells destined to progress to cancer have often accumulated a number of premalignant molecular changes. These changes are sufficiently subtle to require more sensitive, refined genetic analyses for their detection. Therefore, it is important to improve the sensitivity afforded by NAF cytology by examining these cells for chromosomal abnormalities.

SUMMARY OF THE INVENTION

This invention provides a method for studying chromosomal gains and losses in cells from nipple aspirate fluid comprising the steps of:

(1) aspirating fluid from breasts,
(2) placing the samples of fluid obtained in step 1 onto dishes containing conditioned medium composed of a mixture of (a) supernatant from immortalized mammary epithelial cells and (b) mammary epithelial growth medium,
(3) incubating the product of step 2 in a humidified incubator,
(4) replenishing the medium in the dishes prepared in step 2 at regular intervals to maintain cell growth,
(5) isolating the cells from the cultures,
(6) preparing DNA from these cells,
(7) amplifying the DNA,
(8) labeling an aliquot of the amplified DNA, and
(9) evaluating the labeled DNA for evidence of chromosomal gains or losses.

DESCRIPTION OF THE INVENTION

It is the purpose of this invention to provide a novel approach to early detection of premalignant and malignant changes. The use of this testing is particularly important to young women with inherited predisposing factors for breast tumors. The method of the invention uses mammary epithelial cells shed into nipple aspirate fluid to detect cytogenetic abnormalities associated with the early stages of progression toward breast cancer.

The method of the invention is exemplified using molecular cytogenetic methods of comparative genomic hybridization (CGH) to NAF-derived mammary epithelial cells to identify chromosomal gains and losses associated with early breast cancer. CGH permits the rapid screening of chromosomal imbalances within the test genomes without the need for metaphase preparations, only DNA from the test samples is need. While CGH has been exemplified, other methods such as chip technology may also be used in the practice of the invention.

The typical NAF sample from a woman with no breast abnormalities contains less than 10 ductal epithelial cells. Cells in the NAF are a heterogeneous cell population. The epithelial cellularity of NAF increases in the presence of benign or malignant breast abnormalities, as does the likelihood that the woman will secrete NAF. Furthermore, tumor cells are shed more readily than normal cells and probably have a selective growth advantage over normal cells. This could result in a preponderance of abnormal cells in the cultured sample. Chromosomal gains and losses, if present in these cells, can be detected by CGH.

Because NAF tends to contain small numbers of epithelial cells, it is necessary to culture live NAF-derived epithelial cells so that there will be sufficient cells to conduct the necessary cytogenetic studies. The instant method provides means of increasing the number of available cells from a sample to 250 to 500 cells. The DNA from these cells can then be isolated and amplified using means such as the universal DNA amplification procedure, degenerate oligonucleotide primed polymerase chain reaction (DOP-PCR). The combination of culturing NAF-derived cells and use of universal DNA amplification followed by CGH or other means for detection of subtle genomic aberrations in those cells destined to progress to breast cancer can be a valuable diagnostic and screening tool.

MATERIALS AND METHODS

Nipple Aspirate Collection

A modified breast pump comprising a plastic cup attached by a short piece of flexible plastic tubing to a standard 20 ml syringe was used to obtain NAF. The cup is placed over the cleansed nipple of the breast and the woman compresses her breast with both hands while the plunger of the syringe is withdrawn to 10 ml and held for 8–10 seconds. Droplets of fluid that appear at the duct openings on the nipple were collected into capillary tubes. Attempts of 8–10 seconds each were used to obtain the fluid sample.

Cell Culture and DNA Preparation

NAF samples were placed on ice immediately, then transported for processing immediately (within 60 minutes of collection). Samples were plated directly onto a 12 well dish containing conditioned media. The conditioned media is composed equal parts of supernatant from immortalized mammary epithelial cells and mammary epithelial growth medium (MEGM, Clonics, Inc.) to which antibiotics and an antifungal agent have been added. (Kenamycin, Gentamycin and Fungizone were used.) The NAF cells were placed in a humidified incubator with 5% $CO_2$ at 37° C. Cell culture media was added to the NAF cells once every three days.

Colonies of the mammary epithelial cells from the NAF typically emerged within one to two weeks. When sufficient growth had occurred, the cells were trypsinized from the plate surface. The resulting supernatant was then used for genomic DNA extraction.

The example above gives the most common conditions used for cell growth. While exact ratios of components in the culture medium and the conditions may vary, the combination of medium for growth of epithelial cells and supernatant from growing epithelial cell lines has proven particularly useful. Similarly, variation in the amounts and specific identity of antibiotic and anti-fungal agents is appropriate. The exact temperature for incubation may vary somewhat within the parameters usual for growth of tissue cultures. Frequency and timing of addition of culture medium to the growing cells may vary, but usually occurs every 2–5 days.

PCR Amplification

Degenerate oligonucleotide primed polymerase chain reaction as described by Telenius et al. (*Genes Chrom. Cancer* 4: 257–263 (1992) and *Genomics* 13: 718–725 (1992)) was used. The amplification of very small amounts of DNA from a limited number of NAF-derived epithelial cells is possible using the methods, including the culture methods, described herein.

CGH is a cytogenetic technique based on quantitative two color fluorescence in situ hybridization (FISH) as described by Kallioniemi, et al. (*Science* 258: 818–821) and du Manoir, et al. (*Hum. Genet.* 90: 590–610 (1993). Control DNA isolated from an individual with a known normal karyotype and test DNA were labeled with reporter molecules (e.g. digoxigenin d-UTP for control DNA and biotin dUTP for the test DNA), hybridized to normal human metaphases and evaluated with two different fluorochromes (e.g, rhodamine anti-digoxigenin with red fluorescence for digoxigenin labeled control DNA and avidin-FITC with green fluorescence for biotinylated test DNA). The differences in fluorescence intensities along the chromosomes on the normal metaphase reflect the copy number of corresponding sequences in the test DNA. If chromosomes or chromosomal sub-regions are present in identical copy numbers in both the reference and the test genome, the observed fluorescence is a blend of an equal contribution of red and green fluorescence. If chromosomes or chromosomal sub-regions are lost in the test genome, the resulting color is shifted to the red. A gain in any chromosome or chromosomal subregion would be reflected in a more intense green staining on the homologous chromosome in the normal metaphase preparation.

Using the pump as described above, it was possible to obtain NAF from 50% to 70% of the patients.

What we claim is:

1. A method of cytogenetic analysis that comprises evaluating DNA of cultured breast cells obtained from aspirate fluid for evidence of chromosomal gains or losses relative to DNA obtained from a normal breast cell in order to determine the presence or absence of premalignant or malignant breast cells, comprising the steps of:

(1) aspirating fluid containing cells from a breast of a subject that is to be tested for the presence or absence of premalignant or malignant cells in the breast;

(2) placing the samples of fluid obtained in step (1) onto dishes containing conditioned medium composed of (a) supernatant from immortalized mammary epithelial cells and (b) mammary epithelial growth medium;

(3) incubating the product of step (2) in a humidified incubator;

(4) replenishing the medium in the dishes prepared in step (2) at regular intervals to maintain cell growth;

(5) isolating cells from said cultures;

(6) preparing DNA from these cultured cells, as well as reference DNA obtained from normal breast cells;

(7) amplifying the subject DNA, as well as the referenced DNA;

(8) labeling a first aliquot of amplified DNA of the subject cells, and a second aliquot of amplified DNA from the reference normal breast cells; and (9) comparing the labeled DNA of both samples in order to detect chromosomal gains or losses in the subject breast cells, and correlating chromosomal gains or losses to the presence or absence of premalignant or malignant breast cells in the subject.

2. A method of claim 1 wherein the growth medium contains, additionally, antibiotics and anti-fungal agents.

3. A method of claim 1 wherein the ratio of supernatant from immortalized mammary epithelial cell cultures and from mammary epithelial growth medium is about 1:1.

4. A method of claim 1 wherein the incubation temperature is about 37° C.

5. A method of claim 1 wherein the method of amplifying DNA is universal amplification.

6. A method of claim 1 wherein the gains and losses in chromosomal make-up is evaluated using two different fluorochromes.

* * * * *